United States Patent [19]

Kim et al.

[11] 4,151,214

[45] Apr. 24, 1979

[54] PROCESS FOR METHYLATION OF OLEFINS

[75] Inventors: Leo Kim; Milton M. Wald, both of Houston, Tex.

[73] Assignee: Shell Oil Company, Houston, Tex.

[21] Appl. No.: 850,872

[22] Filed: Nov. 14, 1977

[51] Int. Cl.$^2$ .......................... C10G 9/04; C07C 3/56; C07C 5/28; C07C 9/16

[52] U.S. Cl. ................................ 260/676 R; 252/441; 260/682; 260/683.2; 260/683.47; 260/683.68

[58] Field of Search .......... 260/683.47, 676 R, 668 R, 260/666 B

[56] References Cited

U.S. PATENT DOCUMENTS

| | | | |
|---|---|---|---|
| 2,456,584 | 12/1948 | Gorin et al. | 260/668 |
| 2,492,984 | 1/1950 | Grosse et al. | 260/677 X |
| 4,059,646 | 11/1977 | Wald et al. | 260/676 R |
| 4,059,647 | 11/1977 | Wald et al. | 260/676 R |

OTHER PUBLICATIONS

Ansinger, "Mono–Olefins, Chemistry & Technology", 1968, Pergamon Press: p. 736, triptene, triptane.
Malinowski et al., Rocz. Chem. 48 359–360 (1974), "Dimerization & Oligomerization of α-Olefins".

*Primary Examiner*—Delbert E. Gantz
*Assistant Examiner*—G. E. Schmitkons

[57] ABSTRACT

Method for the reaction of an olefin comprising contacting an olefin and a reactant selected from methanol, dimethyl ether, or mixtures thereof, with zinc iodide, zinc bromide, or mixtures thereof, at a temperature of from about 180° C. to 450° C.

13 Claims, No Drawings

PROCESS FOR METHYLATION OF OLEFINS

BACKGROUND OF THE INVENTION

This invention relates to a method for the reaction of olefins by contacting an olefin or olefins with a material such as methanol, dimethyl ether, and mixtures thereof. More particularly, the invention provides a novel process for the production of hydrocarbons, particularly branched chain hydrocarbons, such as triptene and triptane, from olefins and a material selected from methanol, dimethyl ether, or mixtures thereof.

Prior experimental work with methanol conversion to hydrocarbons may be characterized as largely academic or substantially un-economic in present terms. For example, as early as 1878, LeBel and Green (Compt. Rend. vol. 87, p. 260) produced alkyl hydrocarbons by contacting methanol with zinc chloride at elevated temperatures. More recently, Grosse and Snyder describe and claim a process in U.S. Pat. No. 2,492,984 wherein a mixture consisting essentially of a specified metal halide and at least one compound selected from the group consisting of methanol and dimethyl ether is subjected to conversion conditions, including a temperature of 250° C. to 650° C., to form substantial amounts of recoverable hydrocarbons having at least four hydrocarbons. The examples of the patent employ a zinc chloride catalyst, and the specification mentions that higher atomic weight halides of metals such as zinc, cadmium, thorium, and the like, may be used.

The high cost of petroleum-based fuels and the potential availability of large quantities of low cost olefins and methanol, e.g., methanol derived from synthesis gas or methane, have given rise to efforts to convert these materials into higher value products or fuels. For example, because of the superiority of triptane as a blending agent for high-grade gasoline, a process for producing triptane, as well as other hydrocarbons, from olefins and methanol or dimethyl ether could have great economic importance.

SUMMARY OF THE INVENTION

Accordingly, the invention provides a method for reaction of olefins, particularly for the production of hydrocarbons, and especially branched chain hydrocarbons such as triptene and triptane, comprising reacting or contacting an olefin with a material such as methanol, dimethyl ether, or mixtures thereof, and an effective amount of a metal halide selected from zinc iodide, zinc bromide, or mixtures thereof at a temperature of from about 180° C. to about 450° C. In its preferred form, the invention comprises a process for the production of triptene or triptane, wherein an olefin, such as propylene, and methanol are contacted with an effective amount of zinc iodide or zinc bromide at a temperature of from about 190° C. to about 300° C.

The olefins employed in the process are a matter of choice, depending on the products or product mix desired. Thus, where a high proportion of triptane is desired, propylene is suitably employed as the olefin reactant. On the other hand, if isobutylene is utilized as the olefin, a different product mix results. In general, olefins containing 2 to 8 carbon atoms may be employed. Olefins containing 2 to 5 carbon atoms are preferred. Mixtures of olefins may be employed, and impurities, such as minor amounts of alkyl, aromatic or alkynyl hydrocarbons may be present, so long as they (or their reaction products) do not interfere significantly with the desired reaction. Butadiene-(1,3) and other diolefins may be present, but these materials react to provide a different product mix, possibly necessitating additional separation techniques, as set forth in our copending U.S. application entitled Butadiene (1,3) Coversion, filed even date herewith. Refinery and petrochemical streams containing various quantities of these materials are common, and it is an advantage of the invention that such streams may be employed and their contents upgraded to higher value products.

The source of the methanol employed is also a matter of choice. For example, methanol derived from synthesis gas produced from coal, and methanol produced from natural gas are eminently suited to the practice of the invention. The purity of the methanol is not critical, provided the impurities do not interfere with the reaction. Thus, small amounts of water and ethanol, common impurities in methanol, do not interfere. Similarly, the presence of small amounts of synthesis gas from a synthesis gas conversion system does not interfere substantially with the methanol conversion reaction. The degree of purity of the methanol employed will, of course, in the case of certain olefins, affect the quantity of triptene or triptane produced, when considered with respect to total volume of feed material to the reactor, but the decision to use greater purity methanol must be viewed in the light of the increased cost of purification of the methanol prior to use. In general, dilute streams of methanol may be used, provided, as noted, the diluents do not interfere with the activity of the zinc iodide or bromide. The term "methanol", as used in the specification and claims, is intended to include the use of such dilute streams containing methyl alcohol. Moreover, any material which will react to provide methanol in situ under the reaction conditions specified herein, and which does not interfere with the reaction, and whose other reaction product or products, if any, do not interfere with the reaction, is within the scope of the invention. For example, since dimethyl ether may be used as a source of methanol, either as the total feed, or a portion thereof. Under some conditions, disclosed herein, significant quantities of dimethyl ether may be formed. This dimethyl ether may be separated and recycled, thereby providing a highly efficient use of source materials.

In the same manner, the zinc iodide or bromide need not be pure, but may contain impurities which do not interfere with the reaction. Commercial grade zinc bromide and zinc iodide are acceptable in the process of the invention, and mixtures of zinc bromide and zinc iodide may be used.

The temperatures employed in the reaction are significant. In general, the process is suitably carried out at temperatures of from 180° C. to 450° C., with temperatures of 190° C. to 280° C. or 300° C. being preferred. Where triptene or triptane are preferred components of the product mix, lower temperatures are employed. Thus, while triptene and triptane are produced in the presence of zinc iodide at temperatures above 300° C., more significant quantities of triptene and triptane and greater selectivity of the reaction are obtained at temperatures of from 180° C. to 280° C. As indicated, the preferred embodiment range is from about 180° C. to about 280° C., with temperatures of from about 190° C. to about 250° C. being most preferred. Selectivities to triptane are superior, at the general temperatures indicated, and much superior at the preferred temperatures to those obtained at 250° C. or above, even though total quantities of reaction product may be roughly the same or even less.

Pressures employed in the reaction zone are not critical, and may vary widely. Thus, pressures may be atmospheric, below atmospheric, or greater than atmospheric. As a practical matter, pressure in a batch-type system may be atmospheric initially, but will rise as temperatures are raised. Pressures on the order of 2000 psig or even higher may be used, and the selection of the appropriate pressure to be employed is well within the skill of the art.

The ratio of olefin to methanol is widely variable, and those skilled in the art may vary the proportions as desired. Thus, a ratio of 0.1 mols to 25 mols of methanol per mol of olefin may be employed, with a ratio of from 0.3 mols to 10 mols of methanol per mol of olefin being preferred. At the same time, however, the ratio of methanol to $ZnI_2$ or $ZnBr_2$ is significant, and an effective amount of $ZnI_2$, $ZnBr_2$, or mixtures thereof, must be employed. Those skilled in the art may readily determine appropriate amounts, keeping in mind that excessively high ratios of reactants, especially methanol to $ZnI_2$, $ZnBr_2$, or mixtures thereof, may not be used. For example, ratios of from about 0.01 mol of methanol per mol of $ZnI_2$ or $ZnBr_2$ to about 24 mols of methanol per mol of $ZnI_2$ or $ZnBr_2$ may be used, while ratios of from about 0.1 mol of methanol per mol of $ZnI_2$ or $ZnBr_2$ to about 10 mols of methanol per mol of $ZnI_2$ or $ZnBr_2$ are preferred. In the case of mixtures of $ZnI_2$ and $ZnBr_2$, the ratios of mols of "mixture" to methanol are similar, the number of mols of "mixture" being the sum of the number of mols of each component. Where dimethyl ether is used as a feed, the ratio of feed to $ZnI_2$ or $ZnBr_2$ would be similar, and where dimethyl ether is used as a portion of the feed, adjustment of the feed ratio may be made readily.

The process may be conducted batch-wise or in a continuous fashion. Whichever procedure is employed, good mixing or contact of the $ZnI_2$, $ZnBr_2$, or mixture and the reactants is important for good results. Any reaction system which provides a high degree of mixing or contact of reactants may be employed. For example fixed bed systems, slurry reactors, and trickle bed reactors may be used. Contact times are not critical, and those skilled in the art may vary the contact times to provide sufficient contact time to produce optimum results, depending on, e.g., volume of reactants, reactor design, temperature, etc. For example, utilizing a fixed bed reactor design, and continuous flow of reactants, contact times on the order of from about 0.5 minute (245° C.) to about 120 minutes, or 180 minutes, (200° C.), or even longer, may be used. Where batch procedures are employed, contact times may be considerably longer. In both batch and continuous procedure, it is not necessary that 100 percent conversion of the methanol be obtained before recovering the product, the methanol being easily separable and recyclable. Where triptane is the desired product, it may be separated from the other reaction products before use, or the reaction product mixture may be used directly as a fuel or blending agent.

DETAILED DESCRIPTION OF THE INVENTION

In order to describe the invention with greater particularity, reference is made to the following examples:

EXAMPLE 1

About 11.28 grams of 2,3-dimethyl-2-butene, 6.33 grams of methanol, and 32 grams of zinc iodide were placed in a 80-ml Hastelloy B autoclave under 100 psig nitrogen pressure. The reactor was heated to 200° C. for 65 minutes. The reactor was then vented through traps cooled in Dry Ice/acetone mixture. The product analysis is as follows:

| Product | % by weight |
| --- | --- |
| 2,3-dimethyl-1-butene | 15.9% |
| 2,3-dimethyl-2-butene | 43.6% |
| 2,3,3-trimethyl-1-butene (triptene) | 11.6% (1.38g) |
| 2,3,3-trimethyl-butane (triptane) | 5.0% |
| $C_{12}H_{24}$ | 4.4% |
| Other branched hydrocarbons | Remainder |

EXAMPLE 2

Example 1 was repeated with a reaction time of 15 minutes using perdeuterated methanol. Lower olefin conversion resulted, but the reaction produced 55.9% triptene and 5.8% triptane. The extent of deuterium incorporation indicated only one carbon atom in the $C_7$ compounds came from the deuterated methanol.

EXAMPLE 3

Example 1 was repeated using the following reactants and quantities: 200 grams of zinc iodide, 39.8 grams of methanol and 11.5 grams of ethylene. During the reaction time (one hour) the reactor pressure dropped from 800 psi to 310 psig. The results of product analysis are as follows:

| Compound | Weight in Gas (g) | Weight in Liquid | Total Weight (g) |
| --- | --- | --- | --- |
| $H_2$ | 0.0003 | — | — |
| $CH_4$ | 0.010 | — | 0.010 |
| $C_2H_4$ | 2.855 | — | 2.855 |
| $C_2H_6$ | 0.008 | — | 0.008 |
| $C_3$ | 0.150 | — | 0.150 |
| $iC_4H_{10}$ | 1.847 | 1.554 | 3.401 |
| $nC_4H_{10}$ | 0.048 | 0.032 | 0.080 |
| $iC_5H_{12}$ | 0.500 | 1.634 | 2.134 |
| $nC_5H_{12}$ | 0.027 | trace | 0.027 |
| $C_6$ | 0.151 | 1.634 | 0.685 |
| Triptane | 0.056 | 5.825 | 5.881 |
| other $C_7$-$C_8$ | — | 2.156 | 2.156 |
| $C_9$-$C_{15}$ | — | 3.319 | 3.319 |
| $CH_3OH$ | 0.018 | — | — |
| $CH_3OCH_3$ | 0.064 | — | — |
| $CH_3I$ | — | 0.110 | — |

Liquid Hydrocarbon Recovered 16.4g

EXAMPLE 4

Example 1 was repeated using 13 grams of propylene, 25 ml of methanol, and 200 grams of zinc iodide. The reaction was conducted for one hour at 200° C. under 600 psi of carbon monoxide pressure. Only 0.5 grams of unreacted propylene remained. No carbon monoxide was consumed, no esters or carbonyl products were observed.

EXAMPLE 5

Example 1 was repeated using 200 grams of zinc bromide, 25 ml of methanol, and 65 ml 2-methyl-2-butene (2MB-2). The reaction was carried out for one hour at 225° C. The results are summarized as follows:

| Compound | Weight in Gas | Weight in Liquid | Total Weight |
|---|---|---|---|
| $H_2$ | 0.0002 | — | — |
| $CH_4$ | — | — | — |
| $C_2$ | 0.006 | — | 0.006 |
| $C_3$ | — | — | — |
| $iC_4H_{10}$ | 1.567 | 0.763 | 2.330 |
| $iC_5H_{12}$ | 0.289 | 3.062 | 3.351 |
| 2MB-2 | — | 0.052 | 0.052 |
| $C_5H_{10}$ | 0.015 | — | 0.015 |
| $C_6$ | 0.118 | 3.815 | 3.933 |
| Triptane | 0.074 | 1.705 | 1.779 |
| $C_7$-$C_8$ | — | 4.494 | 4.494 |
| $C_9$-$C_{10}$ | — | 5.273 | 5.273 |
| $C_{11}+$ | — | 6.255 | 6.255 |
| $CH_3OCH_3$ | 0.107 | — | — |

Liquid Hydrocarbon Recovered 25.86g

EXAMPLE 6

A one-inch diameter Hastelloy B reactor was packed with a mixture of 15.8 grams of zinc iodide and 0.76 grams of zinc oxide dispersed with carborundum chips. The reactor was heated to 200° C. and a 50:50 mixture of methanol/cyclohexene was passed through at 10 ml/hr.

The product stream contained 77.7% unreacted cyclohexene, 6.2% methyl cyclohexenes and 3.2% dimethyl cyclohexenes.

EXAMPLE 7

Example 5 was repeated except that 64 grams of $ZnI_2$, 35 grams of 2-methyl-2-butene, and 16 grams of methanol were heated at 200° C. for 15 minutes. The major products were triptene (2,3,3-trimethyl-1-butene), and 2,3-dimethyl-butenes.

EXAMPLE 8

Example 4 was followed but isobutane was employed instead of carbon monoxide. In this example, 32.5 grams of methanol, 19.6 grams of isobutane, 19.4 grams of propylene, and 200 grams of $ZnI_2$ were used. Results were similar to those of Example 4.

What is claimed is:

1. A method comprising reacting an olefin with methanol and a catalytically effective amount of a metal halide selected from $ZnI_2$, $ZnBr_2$, and mixtures thereof at a temperature of from 190° C. to 300° C.

2. The method of claim 1 wherein the olefin contains from 2 to 6 carbon atoms.

3. The method of claim 2 wherein the metal halide is $ZnI_2$.

4. The method of claim 2 wherein the metal halide is $ZnBr_2$.

5. The method of claim 2 wherein the metal halide is a mixture of $ZnI_2$ and $ZnBr_2$.

6. A method for the production of triptene comprising reacting 2,3-dimethyl-2-butene with methanol and a catalytically effective amount of a metal halide selected from $ZnI_2$, $ZnBr_2$, and mixtures thereof at a temperature of from 180° C. to 280° C.

7. A method for the production of triptene comprising reacting 2,3-dimethyl-2-butene with methanol and a catalytically effective amount of a metal halide selected from $ZnI_2$, $ZnBr_2$, and mixtures thereof at a temperature of from 180° C. to 280° C.

8. A method comprising reacting an olefin with methanol provided in situ from a material which reacts to provide methanol in situ, other reaction products, if any, being non-interfering, and with a catalytically effective amount of a metal halide selected from $ZnI_2$, $ZnBr_2$, and mixtures thereof, at a temperature of 190° C. to 300° C.

9. The method of claim 11 wherein the material which provides methanol in situ is dimethyl ether.

10. The method of claim 8 wherein the olefin contains from 2 to 6 carbon atoms.

11. The method of claim 10 wherein the metal halide is $ZnI_2$.

12. The method of claim 10 wherein the metal halide is $ZnBr_2$.

13. The method of claim 10 wherein the metal halide is a mixture of $ZnI_2$ and $ZnBr_2$.

* * * * *